United States Patent [19]

Poole et al.

[11] Patent Number: 5,301,261
[45] Date of Patent: Apr. 5, 1994

[54] PRE-INJECTION CHROMATOGRAPHIC SAMPLE SEQUENCER

[75] Inventors: John S. Poole, Landenberg; L. Thompson Staats, III, Lincoln University, both of Pa.

[73] Assignee: Hewlett-Packard Company, Palo Alto, Calif.

[21] Appl. No.: 870,488

[22] Filed: Apr. 16, 1992

Related U.S. Application Data

[63] Continuation of Ser. No. 324,362, Mar. 15, 1989, abandoned.

[51] Int. Cl.$^5$ .................. G06F 9/00; G05D 1/00; B25J 9/00
[52] U.S. Cl. .................. 395/82; 210/360.1; 422/64; 422/67; 422/89
[58] Field of Search ............ 395/82, 84; 210/142, 210/360.1, 782, 360.1; 422/67, 64, 89, 104

[56] References Cited

U.S. PATENT DOCUMENTS

| | | | |
|---|---|---|---|
| 4,235,840 | 11/1980 | Mendoza et al. | 422/64 |
| 4,478,095 | 10/1984 | Bradley et al. | 73/864.21 |
| 4,488,241 | 12/1984 | Hutchins et al. | 395/84 |
| 4,507,044 | 3/1985 | Hutchins et al. | 414/744 R |
| 4,510,684 | 4/1985 | Hutchins et al. | 29/703 |
| 4,578,764 | 3/1986 | Hutchins et al. | 395/84 |
| 4,586,151 | 3/1986 | Buote | 395/84 |
| 4,600,473 | 7/1986 | Friswell | 159/47.1 |
| 4,607,196 | 8/1986 | Abrahams et al. | 318/51 |
| 4,615,226 | 10/1986 | DiNuzzo et al. | 73/864.87 |
| 4,615,902 | 10/1986 | Falcoff et al. | 395/84 |
| 4,632,441 | 12/1986 | Dunlap | 294/1.1 |
| 4,632,631 | 12/1986 | Dunlap | 414/736 |
| 4,689,755 | 8/1987 | Buote | 395/82 |
| 4,697,979 | 10/1987 | Nakashima et al. | 395/82 |
| 4,707,452 | 11/1987 | Friswell | 436/177 |
| 4,713,974 | 12/1987 | Stone | 73/864.23 |
| 4,727,494 | 2/1988 | Buote | 395/82 |
| 4,740,025 | 4/1988 | Nelson | 294/99.1 |
| 4,835,707 | 5/1989 | Amano et al. | 364/497 |
| 4,835,711 | 5/1989 | Hutchins et al. | 395/82 |
| 4,919,887 | 4/1990 | Wakatake | 422/67 |
| 4,927,545 | 5/1990 | Roginski | 422/67 |
| 4,935,875 | 6/1990 | Shah et al. | 364/497 |
| 4,939,095 | 7/1990 | Yokotani | 436/47 |

FOREIGN PATENT DOCUMENTS

| | | |
|---|---|---|
| 0210014 | 1/1987 | European Pat. Off. |
| 2136707 | 12/1972 | France |
| 2528182 | 12/1983 | France |

OTHER PUBLICATIONS

Brochure for "PyTechnology" Systems, Zymark Corporation, Hopkinton, Mass. (1986).
Brochure for HP7673A Automatic Injector, Hewlett-Packard Company, Palo Alto, Calif.
Brochure for HP5890A Gas Chromatograph, Hewlett-Packard Company, Palo Alto, Calif.
Brochure for HP 18587A Bar Code Sample ID System, Hewlett-Packard Company, Nov. 1987.
Zymate Laboratory Automation System, Zymark Corporation, Hopkinton, Mass. (Sep. 1986).
Brochure for HP7673A Automatic Sampler, Hewlett-Packard Company, Palo Alto, Calif.

*Primary Examiner*—Allen R. MacDonald
*Assistant Examiner*—George Davis
*Attorney, Agent, or Firm*—Richard F. Schuette

[57] ABSTRACT

A pre-injection sample sequencing subsystem for laboratory apparatus which includes a chromatograph with a column includes a circular tray with a plurality of concentric arrays of physical locations for storing sample vials in radially extending linear arrays, and a plurality of virtual locations that are extensions of the linear arrays. Each of the physical and virtual locations are individually addressable by a controller for a robot on the tray such that pre-injection sample processing modules may be attached to the tray, located at one or more of the virtual locations. A sequencing method optimizes transfer of samples contained in the vials between their respective physical storage location and the pre-injection processing modules.

7 Claims, 3 Drawing Sheets

PRE-INJECTION CHROMATOGRAPHIC SAMPLE SEQUENCER

This is a continuation of application Ser. No. 324,362, filed Mar. 15, 1989, now abandoned.

BACKGROUND OF THE INVENTION

1. Field of the Invention

This invention relates generally to the field of analytical instrumentation and methods which are useful in chemistry (e.g., spectroscopy and chromatography), and more particularly to laboratory systems as well as subsystems and methods for use with such laboratory systems, including methods for sequencing a plurality of samples through gas or liquid chromatographs, mass spectrometers and the like.

2. Statement of the Prior Art

In the field of chromatography, there are several known systems, subsystems and methods which have been utilized to optimize laboratory analysis of samples with a gas or liquid chromatograph, "PyTechnology TM" systems, manufactured by Zymark Corporation of Hopkinton, Mass., are illustrative of such systems, subsystems and methods.

As is known, "PyTechnology TM" systems incorporate a core system which includes a Zymate II laboratory robot (and controller) that is attached to a central locating plate, around which all other "PySections" are located. The central locating plate is divided into forty-eight sectors, and the hardware for each "PySection" (e.g., a dispenser or a centrifuge) is mounted on a wedge-shaped platform which occupies one or more of the forty-eight sectors.

Illustrative references which describe the robot used in "PyTechnology TM" systems are: U.S. Pat. No. 4,488,241; U.S. Pat. No. 4,507,044; and U.S. Pat. No. 4,510,684; each of which was invented by Hutchins et al., is assigned to Zymark Corporation, and is incorporated herein by reference.

A user of such "PyTechnology TM" systems "teaches" or programs the controller of the desired position for each "PySection", and such positions are automatically stored in the controller as additional "PySections" are added. Once a "PySection" has been put into place, the robot is able to automatically access all working positions on that "PySection" without any additional teaching or programming by the user.

Illustrative references which describe the robot controller used in "PyTechnology TM" systems are: U.S. Pat. No. 4,578,764; U.S. Pat. No. 4,586,151; U.S. Pat. No. 4,689,755; and, U.S. Pat. No. 4,727,494; each of which (with the exception of U.S. Pat. No. 4,578,764 by Hutchins et al.) was invented by Buote, is assigned to Zymark Corporation, and is incorporated herein by reference.

While many prior art laboratory systems, such as the aforedescribed "PyTechnology TM" system of Zymark Corporation, are capable of integration with a gas or liquid chromatographs, they are nevertheless deficient in several aspects. For example, Zymark's "GC Inject PySection" operates with an HP7673A automatic injector, HP5890A gas chromatograph, and HP3392A integrator, each of which is manufactured by Hewlett-Packard Company of Palo Alto, Calif., but lacks the compactness of size which is necessary to ensure quick transfers of samples.

Zymark's "LC Inject PySection" also provides direct injection of prepared samples into an HPLC (i.e., high-performance liquid chromatograph), but it requires that the HPLC be located near the Zymark system which is not within reach of the robot. Furthermore, like many other prior art laboratory systems, the "PyTechnology TM" system utilizes a robot which suffers from the disadvantage of having to be taught.

SUMMARY OF THE INVENTION

Accordingly, it is a general object of the present invention to provide laboratory apparatus for analyzing one or more samples each of which is contained in a respective vial. More specifically, it is an object of the present invention to provide a pre-injection sample sequencing subsystem and method for a laboratory system having chromatographic means which includes a column, a sample port atop the column, means for withdrawing the sample from its respective vial, and means for injecting the withdrawn sample into the column through the sample port.

Another object of the present invention is to provide a pre-injection sample sequencing subsystem and method for such a laboratory system that optimizes the movements of the sample between a storage position, any pre-injection processing positions, and the sample port.

Yet another object of the present invention is to provide a pre-injection sample sequencing subsystem and method for such a laboratory system that improves time-critical analyses performed by the system.

Briefly, these and other objects are accomplished in accordance with the present invention by laboratory apparatus for analyzing one or more samples, each of which is contained in a respective vial. Such apparatus generally comprises chromatographic means for analyzing the samples, means for individually injecting same into a sample port, pre-injection sample processing means for processing preselected ones of the samples, tray means for holding the samples contained in their vials, and robotic means for transferring the samples. The tray means includes a plurality of physical locations each of which is adapted to store a single one of the samples, and a plurality of virtual locations each of which is adapted to juxtapose a single one of the samples to the pre-injection sample processing means. Accordingly, the robotic means includes controller means for sequencing the transfer of the samples between the physical and the virtual locations of the tray means, and the sample port.

In accordance with one important aspect of the present invention, a pre-injection method of sequencing the samples between the physical and virtual locations of the tray means, and the sample port includes not only the steps of providing a circular tray that is attached to the chromatographic means, but also the steps of providing insertable means for holding the plurality of the samples, the holding means including the plurality of physical locations and virtual locations, and also of mounting such holding means to the chromatographic means such that one of the plurality of virtual locations corresponds to the sample port.

In accordance with another important aspect of the present invention, such sample sequencing method further comprises the steps of providing pre-injection sample processing means for processing preselected ones of the samples, adapting each one of the virtual locations to juxtapose each of the samples to the sample processing means, identifying each of the samples and verifying the identification of each such sample prior to its transfer by the robotic means between the physical and virtual locations of the holding means, and the sample port.

Other objects, advantages, and novel features in accordance with the present invention will become more apparent from the following detailed description of a preferred embodiment thereof, considered in conjunction with the accompanying drawings wherein:

DETAILED DESCRIPTION OF THE PREFERRED EMBODIMENT

Figure 1:
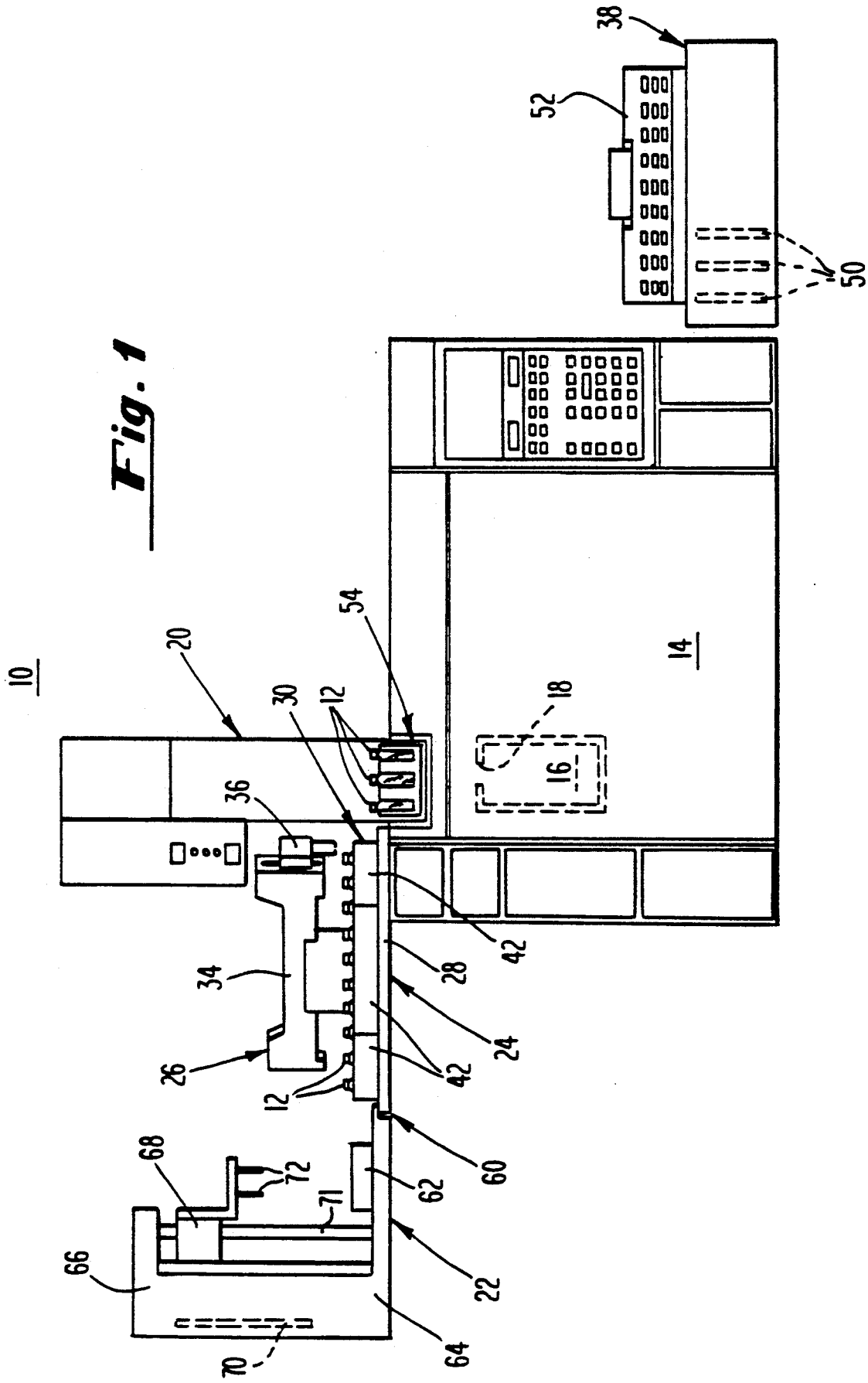
FIG. 1 is a side view of the laboratory apparatus for analyzing samples contained in a vial in accordance with a preferred embodiment of the present invention.

Referring now to the drawings, wherein like numbers designate like or corresponding parts throughout each of the several views, there is shown in FIG. 1 laboratory apparatus 10 for analyzing one or more samples each of which is contained in a respective vial 12.

The apparatus 10 as shown includes chromatographic means 14 for analyzing each of the samples, for example an HP5890A gas chromatograph which is manufactured by Hewlett-Packard Company of Palo Alto, Calif. As is known, such chromatographic means 14 includes a column 16 and a sample port 18 atop the column 16. Such chromatographic means 14, therefore, is generally applicable to both gas and liquid chromatographs.

As such, the chromatographic means 14 facilitates not only the introduction of a sample into a controlled stream of mobile phase at the top of the column 16, but also the continuous monitoring of the column effluent by a suitable detector (i.e., a device transducing chemical information into electrical signals—not shown), followed by a signal recording or by further processing of such recorded information.

The laboratory apparatus 10 further comprises means 20 for individually injecting the samples into the sample port 18, pre-injection sample processing means 22 for processing preselected ones of the samples, tray means 24 for holding the samples contained in their vials 12, and robotic means 26 for transferring the samples between the tray means 24 and the sample port 18.

One suitable such injecting means 20 is an HP7673A automatic on-column injector which is manufactured by Hewlett-Packard Company of Palo Alto, Calif. The precision of such known automatic on-column injecting means 20 is clearly superior to manual injection since variability of injection technique between operators is eliminated. Moreover, sample discrimination is minimized due to fast injection and provisions are made for automated cool on-column capillary injection.

Figure 2:
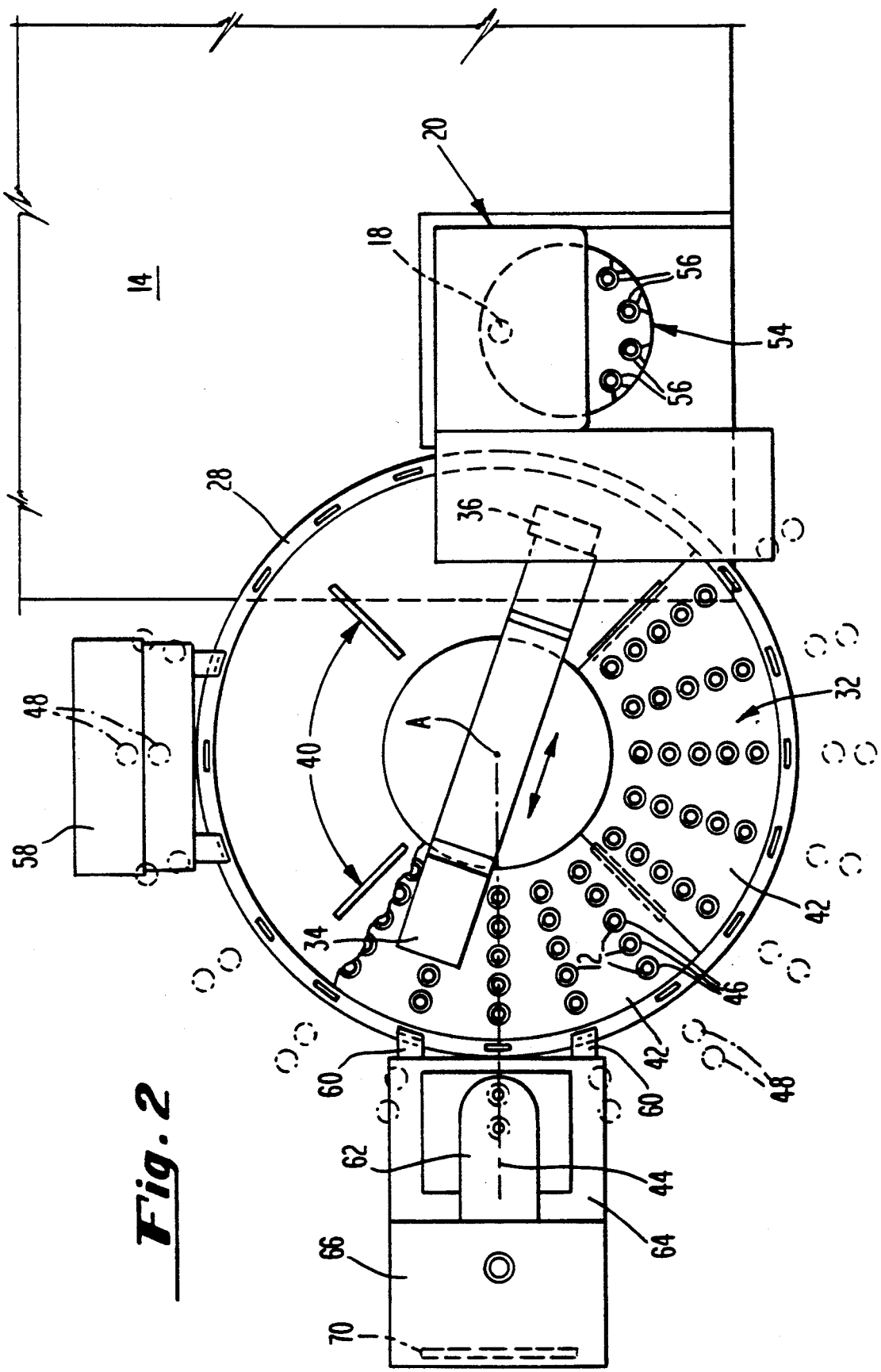
FIG. 2 is a partial top view of the laboratory apparatus shown in FIG. 1.

Referring now also to FIG. 2, it can be seen that the tray means 24 and robotic means 26 suitably comprise an HP7673A automatic sampler which is also manufactured by Hewlett-Packard Company of Palo Alto, Calif. Such tray means 24 includes a circular tray 28 that is attached to the chromatographic means 14, means 30 for holding the samples in a plurality of concentric circular arrays 32, a robotic arm 34 that is adapted to be extended across such circular arrays 32 in the directions of the arrow as shown in FIG. 2, a hand 36, attached to one end of the arm 34, that is adapted to grasp a selected sample contained in its respective vial 12, and means 38 for controlling the transfer of the samples by the robotic means 26.

In accordance with a presently preferred embodiment of this invention, the circular tray 28 is divided into four quadrants 40 in order to support removable inserts 42 which together comprise the holding means 30. Each of the inserts 42 are formed to hold twenty-five vials 12 containing respective samples. Accordingly, while the HP7673A automatic sampler comprising the tray means 24 and the robotic means 26 is operating, the inserts 42 may even be removed or installed without disrupting the sampling sequence. It is readily apparent, therefore, that maximum flexibility in the preparation and loading of samples is provided by the laboratory apparatus 10 as thus far described.

The circular arrays 32 shown in FIG. 2 are formed by a plurality of linear arrays 44 of physical storage locations 46 extending radially outward from a central axis A of the circular tray 28, each one of the physical locations 46 adapted for storage of a single vial 12. Extending further outward from the central axis A from selected ones of the plurality of linear arrays 44 is one or more virtual locations 48, each of which is adapted to juxtapose a single sample-containing vial 12 to the pre-injection sample processing means 22.

Each one of the physical locations 46 and virtual locations 48 is uniquely addressable by the controller means 38. For example, included within the controller means 38 for the pre-injection sample processing means 22 in accordance with a presently preferred embodiment of this invention is one or more circuit boards 50 for purposes of communication with the laboratory apparatus 10. Such controller means 38 may include a typewriter-like keyboard 52, and may be suitably comprised of the HP3393A integrator which is manufactured by Hewlett-Packard Company of Palo Alto, Calif. In accordance with a presently preferred embodiment of this invention, the circuit boards 50 are maintained within a power supply portion 25 of the HP7673A automatic sampler.

In order to position samples for processing within the chromatographic means 14, rotary transfer means 54 is suitably provided with the on-column injecting means 20. Such rotary transfer means 54 temporarily stores a limited number of the samples contained in their vials 12, and juxtaposes a single sample so temporarily stored proximate to the sample port 18. As is shown in FIG. 2, the rotary transfer means 54 comprises a circular array of physical storage locations 56, wherein at least one of the physical storage locations 56 corresponds to one means 30, such that the robotic means 26 can transfer a sample between the tray means 24 and the injecting means 20.

Many chromatographic applications require a certain amount of sample preparation before those samples can be introduced into the chromatograph (e.g., the addition of derivatization agents or internal standards, filtration, dilution, or solid phase extraction). Several of these functions are of a time-critical nature (e.g., heating of a sample to reduce its viscosity, or the addition of derivatization agents), and require certain particular processes to be performed on the sample immediately before its injection into the chromatographic column.

The pre-injection processing means 28 provides such a means.

Identification and verification of the identity of the samples is also the key to accurate chromatographic analyses. Such identification and verification must be performed on each sample both before and after it has been injected into the chromatographic column. Each of the vials 12 in accordance with another important aspect of the present invention includes an encoded label such as a bar code label (not shown) which is human-readable and machine readable. Means 58 is, therefore, provided on the tray means 24 for automatically reading the coded labels on each vial 12. One suitable such means 58 is disclosed in a copending patent application of Engel et al., Ser. No. 142,974, filed Jan. 12, 1988, which is assigned to the assignee of the present invention and is incorporated herein by reference.

In order to perform sample preparation functions, such as heating, the addition of derivatization agents or internal standards, dilution, filtration, or solid phase extraction, the pre-injection processing means 28 of the present invention is mounted to the tray means 24 by one or more mounting brackets 60 and includes a vial holding block 62 upon a base portion 64. The vial holding block 62 has a pair of vial locations corresponding to a pair of virtual locations 48 of the tray means 24. In such a manner, therefore, the vial holding block 62 serves as a location to exchange vials 12 with the adjacent circular tray 28. One of the pair of vial locations on the vial holding block could suitably comprise a hole to dispose of unwanted samples, sample preparation glassware, solid phase extraction columns and filter cartridges. Through the simple insertion of a heater element and temperature sensor (not shown) into the vial holding block 62, the samples which were transferred from the tray means 24 to the pre-injection processing means 28 could be heated at programmed temperatures.

An alternative system could utilize the convective transfer of heat via forced liquid or gas flow through a remotely heated block (not shown) to the vials 12, while a peltier cooler or forced flow of a coolant such as carbon dioxide could be used to allow samples to be cooled. The ability to weigh samples could also be implemented through the addition of a force transducer to the base 64, or by virtue of an analytical balance that would be accessible through the same disposal hole discussed immediately herein above.

An elevator portion 66 is attached to the base portion 64 to provide a means of moving a vertical carriage 68 that is controlled by a circuit board 70. The carriage 68 is movable upwards and downwards upon a lead screw 71 driven by a rotary stepper or DC motor (not shown). Means such as a gripper (not shown) could be used to enable the carriage 68 to grasp, lift, and release vials 12, filters, or solid phase extraction columns.

Alternatively, suitable needles 72 can be installed upon the carriage 68 for various pre-injection sample processing steps. Hollow needles, for example, would permit a dispenser to add or withdraw liquid from the sample vials 12 contained in the vial holding block 62. A heated vial holding block 62 as was briefly discussed herein above would enable high temperature solvation and dilution along with derivatization. Grooved needles, on the other hand, would allow sample vials 12 to be purged with an inert gas. Furthermore, combining this function with a heated vial holding block 62 would also permit a programmed drying of the samples. A cavity (not shown) could also be added below the base portion 64 to enable the rinsing of the needles 72 with solvents pumped from a dispenser to reduce the potential for carryover.

One of the circuit boards 50 suitably comprises a means providing power and communications with the pre-injection processing means 22 which enables the work station 52 to address one or more of the pre-injection processing means 22 via selected commands. An RS-485 communications bus (not shown) is preferably provided between such circuit board 50 and the pre-injection processing means 22.

Another one of the circuit boards 50 comprises a means for interfacing with the work station 52 and other peripherals such as a host computer (not shown). Such interfacing suitably not only provides for overlapping of sample preparation and analysis as described in more detail herein below, but also provides for "token" level control of the on-column injection means 20, tray means 24, and robotic means 26, use of the on-column injection means 20 as a precision dispenser, elimination of any unnecessary "homing" of the robotic means 26 to increase effective speed of the sequencing subsystem, and the ability to manipulate vials 12 of varying sizes. The work station 52 may also include a conventional RS-232C serial interface.

Still another one of the circuit boards 50 suitably comprises a means for controlling operation of the bar code reading means 58. In such a manner, therefore, the pre-injection processing means 22, or any other suitable means for conducting sample preparation functions may be attached directly to the tray means 24, and addressed by the controller means 38 via the virtual locations 48 at which such pre-injection processing means are attached. No teaching of the controller means 38 is necessary.

Figure 3:
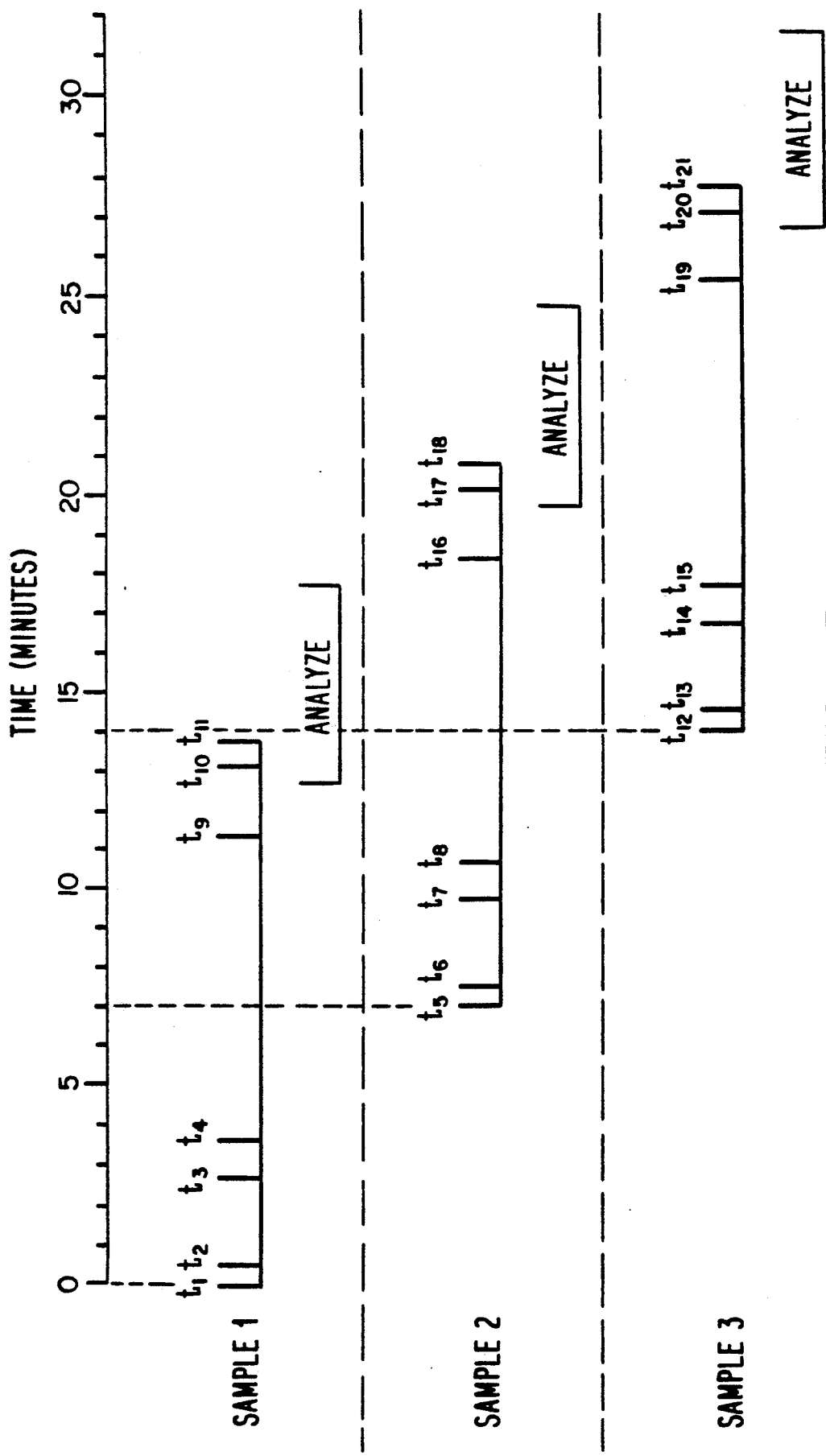
FIG. 3 is a timing diagram of a pre-injection sample sequencing method which utilizes the apparatus shown in FIGS. 1 and 2 in accordance with the preferred embodiment of the present invention.

Referring now to FIG. 3 in conjunction with FIGS. 1 and 2, a pre-injection sample sequencing method which utilizes the aforedescribed apparatus in accordance with the preferred embodiment of the present invention will now be explained.

As noted herein above, it is an object of the present invention to provide a pre-injection sample sequencing subsystem and method for such a laboratory system that optimizes the movements of the sample between a storage position, any pre-injection processing positions, and the sample port. More importantly, however, it is an object of the present invention is to provide a pre-injection sample sequencing subsystem and method for such a laboratory system that improves time-critical analyses performed by the system.

For example, crude oil may contain compounds that are not in solution at room temperature. In order to analyze such samples with a chromatograph for determination as to the existence of those compounds, therefore, the samples would first have to be heated. However, it may be undesirable to store the samples hot as volatile components may be lost. Careful sequencing of the samples through various pre-injection processing steps becomes necessary for accurate chromatographic analysis.

In a laboratory system 10 having chromatographic means 14 for analyzing a sample contained in a vial 12, Wherein the chromatographic means 14 includes a column 16, a sample port 18 atop the column 16, on-column means 20 both for withdrawing the sample from the vial and for injecting the withdrawn sample into the column through the sample port, and means for processing 22 the sample prior to its withdrawal from its vial 12, therefore, a method of sequencing a plurality of the samples between the processing means and the withdrawing and injecting means generally comprises the steps of:

(1) providing a circular tray 28 that is attached to the chromatographic means 14, the circular tray 28 including a central axis A;

(2) providing means for holding 30 the plurality of the samples, the holding means 30 including a plurality of physical locations 46 each of which is adapted for storage of a single vial 12, and a plurality of virtual locations 48 each of which is adapted to juxtapose a single vial 12 with the processing means 22;

(3) mounting the holding means 30 to the chromatographic means 14 such that one of the plurality of virtual locations 48 is proximate to the sample port 18;

(4) providing robotic means 26, including an arm 34 an a hand 36 attached to the arm 34, for transferring a single vial 12 between its respective physical location 46 and selected ones of the plurality of virtual locations 48 including the sample port 18; and, (5) controlling the robotic means 26 to optimize movement thereof for transferring a single vial 12 between its respective physical location 46 and the selected ones of said plurality of virtual locations 48.

The step of providing the holding means 30 suitably comprises the steps of: providing more than one circular array 32 of the physical locations 46 which are disposed concentrically about the central axis A; disposing each physical location 46 in a respective one of the circular arrays 32 in a linear array 44 of the physical locations 46 extending radially outward from the central axis A; and disposing each one of the virtual locations 48 as an extension of one of the linear arrays 44.

As was explained herein above with reference to the laboratory apparatus 10, the method according to a presently preferred embodiment further comprises the step of providing the on-column means 20 with rotary transfer means 54 for temporarily storing a limited number of samples contained in their vials 12, and for juxtaposing a single one of that limited number of samples so temporarily stored proximate to the sample port 18. The rotary transfer means 54 may preferably comprise a circular array of physical storage locations 56, wherein at least one of those storage locations 56 of the circular array 54 in the rotary transfer means 54 corresponds to one of the plurality of virtual locations 48 of the holding means 30.

As is best illustrated by FIG. 3, the controlling step of the sequencing method according to the present invention comprises the steps of:

(a) assigning a unique address to each one of the physical and virtual locations 46, 48 of the holding means 30;

(b) instructing the robotic means 26 via the circuit cards 50 to retrieve a selected sample from its respective physical location 46;

(c) retrieving the selected sample with the robotic means 26;

(d) instructing the robotic means 26 to transfer the selected sample from its respective physical location 46 to the processing means 22;

(e) transferring the selected sample with the robotic means 26 to the processing means 22;

(f) instructing the processing means 22 to conduct at least two pre-injection processing steps upon the selected sample;

(g) conducting one of the at least two pre-injection processing steps upon the selected sample with the processing means 22;

(h) conducting other ones of the at least two pre-injection processing steps upon selected sample with the processing means 22;

(i) instructing the robotic means 26 to retrieve another selected sample from its respective physical location 46;

(j) retrieving the other selected sample with the robotic means 26 during the conduct of the other pre-injection processing steps on a previously selected sample;

(k) instructing the robotic means 26 to transfer the other selected sample to the processing means 22;

(l) transferring the other selected sample with the robotic means 26 to the processing means 22 during the conduct of said other pre-injection processing steps on the previously selected sample;

(m) instructing the robotic means 26 to retrieve the previously selected sample from the processing means 22 upon completion of the other pre-injection processing steps;

(n) retrieving the previously selected sample with the robotic means 26 from the processing means 22 upon completion of the at least two pre-injection processing steps;

(o) instructing the robotic means 26 to transfer the previously selected sample to the virtual location 48 of the holding means 30 that corresponds to the at least one of said physical storage locations 56 of the circular array in the rotary transfer means 54;

(p) transferring the previously selected sample with the robotic means 26 to the virtual location 46 of the holding means 30 that corresponds to the at least one of the physical storage locations 56 of the circular array in the rotary transfer means 54;

(q) instructing the rotary transfer means 54 to transfer the previously selected sample to the sample port 18;

(r) instructing the on-column means 20 to withdraw the previously selected sample from its vial 12;

(s) instructing the on-column means 20 to inject the withdrawn sample into the column 16 through the sample port 18; and (t) repeating steps (f) through (s) for the other selected sample The method according to this presently preferred embodiment of this invention, may further comprise the steps of: identifying each selected sample (e.g., by a bar code label); instructing the robotic means 26 to transfer the selected sample to the processing means 22 by communication of its unique address; rotating the arm 34 about the central axis A to align the hand 36 with the particular one of the linear arrays 44 that corresponds to the selected sample; extending the hand 36 to the physical location 46 of the holding means 30 that corresponds to the selected sample; grasping the selected sample with the hand 36; and verifying the identity of each selected sample prior to its transfer to the processing means 22. Such verification may be suitably performed in accordance with the method and apparatus described in copending Ser. No. 142,974.

For a plurality of such samples, referring now more specifically to FIG. 3, the sequencing method according to the present invention takes a first sample with the robotic means 24 and places it in the bar code reading means 58 where the bar code label (not shown) on the vial 12 of the first selected sample is read at time t1.

After verification by the controller means 38, the first sample is taken to the pre-injection processing means 22 where, for example, a solvent could be dispensed at time t2 through the needles 72 into that first sample.

Thereafter, at the pre-injection processing means 22 or other suitable such means that are disposed at other virtual locations 48 around the tray means 24, the first sample would be agitated at time t3 and heated for a period of time commencing at time t4, any necessary transfer of the first sample being performed by the robotic means 26.

While the first sample is completing the heating step, the robotic means 26 would take another sample and transfer it to the bar code reading means 58 where the bar code label (not shown) on the vial 12 of the second selected sample would be read at time t5. Thereafter, similar dispensing, agitation and heating pre-injection processing steps would be performed respectively on the second sample at times t6, t7 and t8. In order to then optimize such pre-injection processing, the first sample would be retrieved by the robotic means 26, transferred to the virtual location 48 corresponding to the rotary transfer means 54 of the on-column injection means 20, rotated by such rotary transfer means 54 to the sample port 18 and be injected at time t9 into the column 16. The first sample vial 12 would then be discarded at time t10, and the robotic means 26 would be returned to a "home" position at time t11.

Almost immediately thereafter, and while the second sample was still being heated, a third sample could be retrieved by the robotic means 26 and transferred to the bar code reading means 58 where the bar code label (not shown) on the vial 12 of that third selected sample would be read at time t12. Again, similar dispensing, agitation and heating pre-injection processing steps would be performed respectively on the third sample at times t13, t14 and t15. In order to continue optimizing such pre-injection processing, the second sample would be retrieved by the robotic means 26, transferred to the virtual location 48 corresponding to the rotary transfer means 54 of the on-column injection means 20, rotated by such rotary transfer means 54 to the sample port 18 and be injected at time t16 into the column 16. The second sample vial 12 would then be discarded at time t17, and the robotic means 26 would be returned to its "home" position at time t18.

Obviously, many modifications and variations of the present invention are possible in light of the foregoing teachings. It is to be understood, therefore, that within the scope of the appended claims, the present invention may be practiced otherwise than as is specifically disclosed herein.

What we claim is:

1. In a laboratory system having chromatographic means for analyzing a sample contained in a vial, wherein the chromatographic means includes a column, a sample port atop the column, on-column means both for withdrawing the sample from the vial and for injecting the withdrawn sample into the column through the sample port, wherein the system includes a processing means for processing the sample prior to its withdrawal from its vial, a method of sequencing a plurality of samples between the processing means and the withdrawing and injecting means, comprising the steps of:

holding a plurality of samples using a circular tray that is attached to the chromatographic means, said circular tray including a central axis, wherein the tray comprises a plurality of physical locations each of which is adapted for storage of a single vial;

defining a plurality of virtual locations, one of which is adapted to juxtapose a vial with the processing means and one of which is adapted to juxtapose a vial with the sample port;

mounting said tray to the chromatographic means such that one of said plurality of virtual locations is proximate to the sample port;

transferring a vial using a robot means between its respective physical location and selected ones of said plurality of virtual locations including at least the sample port; and controlling said robot means to optimize movement thereof for transferring a single vial between its respective physical location and said selected ones of said plurality of virtual locations.

2. The method according to claim 1, wherein said step of holding comprises the steps of:

using more than one circular array of said plurality of physical locations disposed concentrically about said central axis;

disposing each said physical location in a respective one of said more than one circular arrays in a linear array of said plurality of physical locations extending radially outward from said central axis; and disposing each one of said plurality of virtual locations as an extension of one of said linear arrays.

3. The method according to claim 1, further comprising the step of using the withdrawing and injecting means with rotary transfer means for temporarily storing a limited number of said plurality of samples, and for juxtaposing a single one of said limited number of samples so temporarily stored proximate to said sample port, said rotary transfer means comprising a circular array of physical storage locations, wherein at least one of said physical storage locations of said circular array in said rotary transfer means corresponds to one of said plurality of virtual locations of said holding means.

4. The method according to claim 3, wherein said controlling step comprises the steps of:

(a) assigning a unique address to each one of the physical and virtual locations of said holding means;

(b) instructing said robot means to retrieve a selected sample from its respective physical location;

(c) retrieving said selected sample with said robot means;

(d) instructing said robot means to transfer said selected sample from its respective physical location to the processing means;

(e) transferring said selected sample with said robot means to the processing means;

(f) instructing the processing means to conduct at least two pre-injection processing steps upon said selected sample;

(g) conducting one of said at least two pre-injection processing steps upon said selected sample with the processing means;

(h) conducting other ones of said at least two pre-injection processing steps upon said selected sample with the processing means;

(i) instructing said robotic means to retrieve another selected sample from its respective physical location;

(j) retrieving said other selected sample with said robot means during the conduct of said other pre-injection processing steps on a previously selected sample;

(k) instructing said robot means to transfer said other selected sample to the processing means;

(l) transferring said other selected sample with said robot means to the processing means during the conduct of said other pre-injection processing steps on said previously selected sample;

(m) instructing said robot means to retrieve said previously selected sample from the processing means upon completion of said other pre-injection processing steps;

(n) retrieving said previously selected sample with said robot means from the processing means upon completion of said at least two pre-injection processing steps;

(o) instructing said robot means to transfer said previously selected sample to said virtual location of said holding means that corresponds to said at least one of said physical storage locations of said circular array in said rotary transfer means;

(p) transferring said previously selected sample with said robot means to said virtual location of said holding means that corresponds to said at least one of said physical storage locations of said circular array in said rotary transfer means;

(q) instructing said rotary transfer means to transfer said previously selected sample to the sample port;

(r) instructing the on-column means to withdraw said previously selected sample from its vial;

(s) instructing the on-column means to inject said withdrawn sample into the column through the sample port; and (t) repeating steps (f) through (s) for said other selected sample.

5. The method according to claim 4, further comprising the steps of:

identifying each said selected sample;

instructing said robot means to transfer said selected sample to the processing means by communication of its unique address;

rotating said arm about said central axis to align said hand with the particular one of said linear arrays that corresponds to said selected sample;

extending said hand to said physical location of said holding means that corresponds to said selected sample;

grasping said selected sample with said hand; and verifying the identity of each said selected sample prior to its transfer to the processing means.

6. A method of sequencing one or more samples in an analytical apparatus, wherein the analytical apparatus comprises: (a) a chromatograph that includes a sample port; and (b) a pre-injection sample processing means for processing preselected ones of the one or more samples, the method comprising the steps of:

transferring a vial using a robot means;

controlling the robotic system to transfer at least one of the samples to a tray that includes a plurality of physical locations for storing samples;

defining a plurality of virtual locations outside the tray that include at least one of the pre-injection sample processing means and the sample port;

controlling the robotic system to selectively transfer a first sample to one of the virtual locations; and controlling the robotic system to optimize transferring a plurality of vials between their respective physical location and the virtual locations, whereby a second vial is transferred while a first vial is disposed in a virtual location.

7. The method of claim 6 wherein the steps of transferring at least one of the vials to one of the virtual locations comprises programming a controller for controlling a manipulator.

* * * * *